US009850538B2

(12) United States Patent
Jayaraman

(10) Patent No.: US 9,850,538 B2
(45) Date of Patent: Dec. 26, 2017

(54) METHODS FOR DIAGNOSING AND TREATING DIABETES

(71) Applicant: The Board of Trustees of the University of Illinois, Urbana, IL (US)

(72) Inventor: Sundararajan Jayaraman, Darien, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/684,707

(22) Filed: Apr. 13, 2015

(65) Prior Publication Data

US 2016/0298191 A1 Oct. 13, 2016

(51) Int. Cl.
C12Q 1/68 (2006.01)

(52) U.S. Cl.
CPC ..... *C12Q 1/6883* (2013.01); *C12Q 2600/158* (2013.01)

(58) Field of Classification Search
None
See application file for complete search history.

(56) References Cited

PUBLICATIONS

Bonifacio et al. "A Strategy to find Gene Combinations that Identify Children who Progress Rapidly to Type 1 Diabetes After Islet Autoantibody Seroconversion" Acta Diabetol. 2014 51:403-11.
Hisanaga-Oishi, et al. "Analysis of the Expression of Candidate Genes for Type 1 Diabetes Susceptibility in T Cells" Endocr. J. 2014 61:577-88.
Jayaraman, A.K. & Jayaraman, S. "Increased Level of Exogenous Zinc Induces Cytotoxicity and Up-regulates the Expression of the ZnT-1 Zinc Transporter Gene in Pancreatic Cancer Cells" J. Nutr. Biochem. 2011 22:79-88.
Jayaraman et al. "Transcriptome Analysis of Epigenetically Modulated Genome Indicates Signature Genes in Manifestation of Type 1 Diabetes and its Prevention in NOD Mice" PLoS One 2013 8:e55074.
Jayaraman, S. "Novel Methods of Type 1 Diabetes Treatment" Discov. Med. 2014 17:347-355.
Patel et al. "Chromatin Remodeling Rests the Immune System to Protect Against Autoimmune Diabetes in Mice" Immunol. Cell Biol. 2011 89:640-649.

*Primary Examiner* — Joseph G. Dauner
(74) *Attorney, Agent, or Firm* — Licata & Tyrrell P.C.

(57) ABSTRACT

Methods and kits for diagnosing and treating type I diabetes based upon the expression of macrophage-specific Chymotrypsin-Like Elastase Family, Member 3B, either alone or in combination with sialic acid-binding immunoglobulin-like lectin-1, are provided.

6 Claims, 1 Drawing Sheet

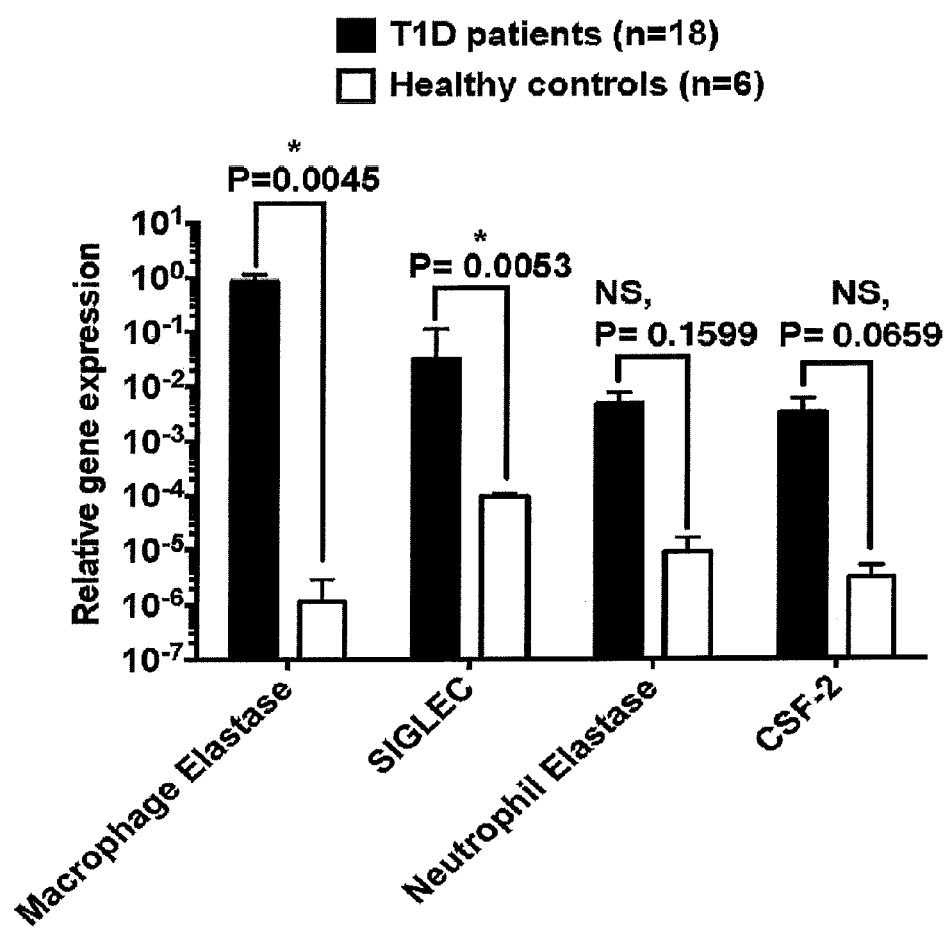

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 1
gcaagatgcc tgactttccc                                              20

<210> SEQ ID NO 2
<211> LENGTH: 21
<212> TYPE: DNA
<213> ORGANISM: Artificial Sequence
<220> FEATURE:
```

<223> OTHER INFORMATION: Synthetic oligonculeotide

<400> SEQUENCE: 2
cccgaaagtg gaattcacag g                                             21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 3
taggcccggg tgtaggattc                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 4
gaattgccca tccgtaccct                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 5
gccaagtctg atctccgtgc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 6
gacaatctct cccgcccttc                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 7
ccaggccagg aagtccaaac                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 8
ggcccttatc agccacacat                                               20

```
<210> SEQ ID NO 9
<211> LENGTH: 24
<212> TYPE: DNA
<213> ORGANISM: Artificial Sequence
<220> FEATURE:
<223> OTHER INFORMATION: Synthetic oligonculeotide

<400> SEQUENCE: 9
aggacgaaca tccaaccttc ccaa                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonculeotide

<400> SEQUENCE: 10
tttgagccag aagaggttga gggt                                              24

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonculeotide

<400> SEQUENCE: 11
gagatgcctt gggttcagtg attg                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonculeotide

<400> SEQUENCE: 12
ggtcagggaa acatggattc acac                                              24

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 13
agggagctct gacttgacca                                                   20

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonculeotide

<400> SEQUENCE: 14
gggacagcct ttttatgggg a                                                 21

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonculeotide
```

<400> SEQUENCE: 15
gtaagtgacc acagaaggag aaa                                                   23

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 16
cccaggagtc atcgttgttt                                                       20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 17
tgttcgtact gtccaggtga                                                       20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 18
gaagggaggt gggtagcaaa                                                       20

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonculeotide

<400> SEQUENCE: 19
tggtgcagag cgattattca gg                                                    22

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 20
taacagcagc catgagggtt                                                       20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 21
cgcatcctta cctctgtccc                                                       20

<210> SEQ ID NO 22
<211> LENGTH: 20

-continued

```
<212> TYPE: DNA
<213> ORGANISM: Artificial Sequence
<220> FEATURE:
<223> OTHER INFORMATION: Synthetic oligonculeotide

<400> SEQUENCE: 22
accccagcat ttgccgaata                                             20

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonculeotide

<400> SEQUENCE: 23
actggaagcc tggaagttta g                                           21

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 24
acctcctctc agacaaagga                                             20

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonculeotide

<400> SEQUENCE: 25
ggtggtgact ggcgtgcta                                              19

<210> SEQ ID NO 26
<211> LENGTH: 17
<212> TYPE: DNA
<213> ORGANISM: Artificial Sequence
<220> FEATURE:
<223> OTHER INFORMATION: Synthetic oligonculeotide

<400> SEQUENCE: 26
ccactgcgca gctggaa                                                17

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonculeotide

<400> SEQUENCE: 27
cactccaggc actgttcata a                                           21

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 28
```

-continued

```
taaccgagac accagcaaag                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 29
gcctgcatta ggaggtcttt                                              20

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonculeotide

<400> SEQUENCE: 30
cctgacacca gcaaaggata a                                            21

<210> SEQ ID NO 31
<211> LENGTH: 22
<212> TYPE: DNA
<213> ORGANISM: Artificial Sequence
<220> FEATURE:
<223> OTHER INFORMATION: Synthetic oligonculeotide

<400> SEQUENCE: 31
cgatatgaac cacctggaga gg                                           22

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 32
acggagtcag attttcccccg                                             20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 33
ccacaagccc tctgagagtc                                              20

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonculeotide

<400> SEQUENCE: 34
ttgacaaggt gtggccaag                                               19

<210> SEQ ID NO 35
<211> LENGTH: 20
<212> TYPE: DNA
<213> ORGANISM: Artificial Sequence
```

```
<220> FEATURE:
<223> OTHER INFORMATION: Synthetic oligonculeotide

<400> SEQUENCE: 35
agttcacagt cagcctgcat                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonculeotide

<400> SEQUENCE: 36
caggtgagat tccgcaaagc                                          20
```

METHODS FOR DIAGNOSING AND TREATING DIABETES

BACKGROUND

Type I diabetes (T1D) afflicts 29.1 million people and 9.3% of the United States population. In spite of increased awareness and improved living conditions, and the distribution of similar risk (HLA) genes, T1D has been rising recently at an alarming rate in the world, and especially in the Scandinavian countries, among children. T1D is recognized as an autoimmune disease mediated by T lymphocytes in individuals with genetic predisposition. Despite decades of research, the details of the mechanisms involved in the manifestation of T1D remain sketchy. Many clinical trials have been conducted aiming at the prevention of the onset as well as halt the progression of T1D. These include induction of oral tolerance against insulin, reduced exposure to dietary components such as cow's milk and gluten, blocking the availability of cytokines and other mediators that can potentially cause damage to beta cells using antibodies, and reducing the frequency of autoreactive T lymphocytes by administering antibody against the T cell receptor and other accessory components. However, all of these attempts have met with little or no success for the alleviation of T1D. The failure of these various attempts to intervene the progression of T1D in seropositive individuals is primarily attributed to the poor understanding of the disease process resulting in the inability to pinpoint the time and method of intervention for effective control of T1D.

In addition to the poor understanding of the underlying mechanisms of T1D, the lack of robust diagnostic tests confounds early diagnosis and treatment of this disease. The only available diagnostic test to date is the detection of antibodies against insulin (IAA), glutamic acid decarboxylase (GADA), insulinoma antigen 2 (IA-2A), and zinc transporter 8 (ZNT8A), using expensive and radioactive methods, which are not easily accessible to the general public (Jayaraman (2014) Discov. Med. 17:347-355). HLA genotypes such as HLA DR3/4 are considered to contribute to the susceptibility for developing diabetes. However, these HLA genotypes provide an expected diabetes risk of about 10% in first-degree relatives and therefore are not very reliable in predicting the development of T1D in high-risk individuals. In addition, >50 non-HLA associated regions have been implicated in contributing weak-to-moderate susceptibility to T1D. This was based on determining the single nucleotide polymorphisms (SNPs) in genetic loci revealed by genome-wide association studies (GWAS). However, it is unclear how these SNPs in these loci, each composed of multiple genes, can influence disease outcome. Therefore, these loci do not serve as reliable biomarkers for disease diagnosis or progression. Although these SNPs may indicate the propensity to develop T1D, they cannot be used as biomarkers for the predicting the development of overt diabetes in seropositive individuals (Jayaraman (2014) Discov. Med. 17:347-355).

There are several problems associated with existing antibody detection as a diagnostic test. First, less than 30% of individuals with the genetic predisposition (HLA DR3/4 expression) develop autoantibodies. In addition, occurrence of full-blown diabetes takes a number of years after the appearance of autoantibodies. Further, some individuals, especially Southeast Asians, develop T1D without any sign of autoantibodies. Moreover, it is the T lymphocytes, and not the antibodies, that have been implicated in the destruction of beta cells in T1D. As such, reliability of antibody tests for the diagnosis and prognosis of T1D is questionable.

Recently, a few other biomarkers have been proposed for the detection of T1D, such as differentially expressed genes in the peripheral blood (Bonifacio, et al. (2014) Acta Diabetol. 51:403-11) as determined by microarrays. Whereas the gene expression profiling represents a new line of thinking to find suitable biomarkers for T1D, the selection of genes did not permit the stratification of these patients (Bonifacio, et al. (2014) Acta Diabetol. 51:403-11). Another report necessitated the isolation of subsets of T lymphocytes for microarray analysis (Hisanaga-Oishi, et al. (2014) Endocr. J. 61:577-88). However, this study suffers from a number of shortcomings. Besides being expensive, this analysis is also impractical to perform in a large cohort of patients as a cross-sectional study as well as a longitudinal investigation to correlate the relationship between the expression of certain genes and the onset and/or progression of T1D. Finally, although T1D is considered to be initiated by autoreactive T lymphocytes, recent work has indicated the participation of the innate immune system as well (Jayaraman (2014) Discov. Med. 17:347-355). Therefore, ideal biomarkers should include genes that are over-expressed by T cells as well as the innate immune system under the diabetic condition. Compromised expression of genes implicated in affording protection against diabetes may serve as additional biomarkers for determining the susceptibility to develop diabetes.

SUMMARY OF THE INVENTION

This invention provides methods for diagnosing and treating a subject diagnosed with type I diabetes by obtaining a sample from the subject; measuring the expression of Chymotrypsin-Like Elastase Family, Member 3B (CELA3B) and optionally sialic acid-binding immunoglobulin-like lectin-1 (SIGLEC-1) protein, or nucleic acids encoding the same, in the sample; comparing the expression of CELA3B and optionally SIGLEC-1 in the sample to the expression of CELA3B and optionally SIGLEC-1 in a control; and diagnosing and optionally treating the subject for diabetes when the expression of CELA3B and optionally SIGLEC-1 in the sample from the subject is elevated compared to the expression of CELA3B and optionally SIGLEC-1 in the control. In certain embodiments, the expression of CELA3B is measured using oligonucleotides of SEQ ID NO:1 and SEQ ID NO:2. In other embodiments, the expression of SIGLEC-1 is measured using oligonucleotides of SEQ ID NO:3 and SEQ ID NO:4. Kits containing oligonucleotides of SEQ ID NO:1 and SEQ ID NO:2 and optionally oligonucleotides of SEQ ID NO:3 and SEQ ID NO:4 are also provided.

BRIEF DESCRIPTION OF THE DRAWINGS

FIG. 1 shows the overexpression of selected inflammatory genes in patients with type I diabetes (T1D) as compared to healthy control subjects. NS, not statistically significant. Macrophage Elastase, Chymotrypsin-Like Elastase Family, Member 3B (CELA3B); SIGLEC, sialic acid-binding immunoglobulin-like lectin-1; Neutrophil Elastase, ELANE; CSF2, Colony Stimulating Factor 2.

DETAILED DESCRIPTION OF THE INVENTION

It has now been found that macrophage-specific Chymotrypsin-Like Elastase Family, Member 3B (CELA3B), either alone or in combination with sialic acid-binding immunoglobulin-like lectin-1 (SIGLEC-1), can be used to in the diagnosis and/or prognosis of T1D. In particular, the expression of CELA3B and SIGLEC-1 has been shown to be elevated in subjects with T1D as compared to healthy subjects. Therefore, CELA3B and SIGLEC-1 serve as biomarkers for assessing the susceptibility of a subject to develop T1D as well as help to define the rate of progression to full-blown diabetes during asymptomatic phase. The measurement of these markers, alone or in combination, in subject samples provides information that the diagnostician can correlate with a diagnosis of type I diabetes or risk of developing type I diabetes so that a treatment plan for the subject can be established. In addition to diagnosis, these biomarkers can be used as potentially therapeutic targets for treatment of type I diabetes.

A biomarker is an organic biomolecule, the presence of which in a sample is used to determine the phenotypic status of the subject (e.g., diabetes patient v. normal patient). In a preferred embodiment, the biomarker is differentially expressed in a sample taken from a subject of one phenotypic status (e.g., having a disease) as compared with another phenotypic status (e.g., not having the disease). Biomarkers, alone or in combination, provide measures of relative risk that a subject belongs to one phenotypic status or another. Therefore, they are useful as markers for disease (diagnostics), therapeutic effectiveness of a drug (theranostics), drug toxicity, and predicting and identifying the immune response. In some embodiments, the biomarker is CELA3B, or a fragment or variant thereof. In other embodiments, the biomarkers are CELA3B and SIGLEC-1, or fragments or variants thereof.

Macrophage-specific chymotrypsin-like elastase family, member 3B (CELA3B), also known as E1, CBPP, EL-1 and ELA3B, belongs to the subfamily of serine proteases that hydrolyze many proteins in addition to elastin. Humans have six elastase genes which encode the structurally similar proteins elastase 1, 2, 2A, 2B, 3A, and 3B. Unlike other elastases, elastase 3B has little elastolytic activity. Like most of the human elastases, elastase 3B is secreted from the pancreas as a zymogen and, like other serine proteases such as trypsin, chymotrypsin and kallikrein, it has a digestive function in the intestine. Elastase 3B preferentially cleaves proteins after alanine residues and has been suggested to function in intestinal transport and metabolism of cholesterol. The nucleic acid sequence encoding CELA3B is known in the art under GENBANK Accession No. NM_007352. Similarly, the amino acid sequence of the CELA3B protein is known under GENBANK Accession No. NP_031378. Primers for assessing the expression of CELA3B can be prepared using the nucleic acid sequence encoding CELA3B or using primers known in the art. For example, the $RT^2$ qPCR Primer Assay for Human CELA3B (Qiagen; Valencia, Calif.) or qSTAR qPCR primer pairs against *Homo sapiens* gene CELA3B (Origene; Rockville, Md.) can be used in the method described herein.

Sialic acid-binding immunoglobulin-like lectin (SIGLEC) is characterized by a homologous N-terminal V-set Ig-like domain and between one (CD33) and 16 (sialoadhesin) C2-set Ig-like domains (Crocker & Varki (2001) *Trends Immunol.* 22:337-342; Crocker & Varki (2001) *Immunology* 103:137-145; Crocker (2002) *Curr. Opin. Struct. Biol.* 12:609-615). In humans, 11 members of the Siglec family have been identified: sialoadhesin (Siglec-1, CD169), CD22 (Siglec-2), the myelin-associated glycoprotein (Siglec-4, MAG), and additional members, which constitute a subgroup including CD33 (Siglec-3) and CD33-related Siglecs (Siglec-5 to -11) (Crocker & Varki (2001) *Immunology* 103:137-145; Cornish, et al. (1998) *Blood* 92:2123-32). Siglecs are found on the surface of cells of the hematopoietic system, with the exception of Siglec-4, which is also expressed by oligodendrocytes and Schwann cells in the nervous system (Arquint, et al. (1987) *Proc. Natl. Acad. Sci. USA* 84:600-604). SIGLEC-1 expression by CD14+ monocytes is significantly increased in multiple sclerosis patients compared with controls (Malhotra, et al. (2013) *Mult. Scler.* 19(5):524-31). Elevated SIGLEC-1 expression in PBMCs and monocytes can potentially serve as a biomarker for monitoring disease activity in rheumatoid arthritis. SIGLEC-1 may also play a proinflammatory role in stimulating lymphocyte proliferation and activation in rheumatoid arthritis (Xiong, et al. (2014) *Rheumatology (Oxford)* 53(2):250-9). The nucleic acid sequence encoding SIGLEC-1 is known in the art under GENBANK Accession No. NM_023068. Similarly, the amino acid sequence of the SIGLEC-1 protein is known under GENBANK Accession No. NP_075556. Primers for assessing the expression of SIGLEC-1 can be prepared using the nucleic acid sequence encoding SIGLEC-1 or using primers known in the art. For example, the $RT^2$ qPCR Primer Assay for Human SIGLEC-1 (Qiagen; Valencia, Calif.) or qSTAR qPCR primer pairs against *Homo sapiens* gene SIGLEC-1 (Origene; Rockville, Md.) can be used in the method described herein.

Using the biomarker(s) described herein, the present invention provides methods for diagnosing and treating type I diabetes in a subject having, suspected of having, or at risk of having type I diabetes by measuring the expression level of CELA3B and optionally SIGLEC-1. In accordance with the diagnostic method, a sample is obtained from a subject; the expression of CELA3B and optionally SIGLEC-1 protein, or nucleic acids encoding the same, is measured in the sample; the expression level or amount of CELA3B and optionally SIGLEC-1 in the sample is compared to the expression level or amount of CELA3B and optionally SIGLEC-1 in a control, e.g., one or more normal, i.e., non-diabetic samples obtained from one or more non-diabetic individuals and the subject is diagnosed with type I diabetes when the expression of CELA3B and optionally SIGLEC-1 in the sample from the subject is elevated compared to the expression of CELA3B and optionally SIGLEC-1 in the control. In one embodiment, the assay of the present invention is carried out by measuring the expression level or amount of CELA3B. In another embodiment, the assay of the present invention is carried out by measuring the expression level or amount of both CELA3B and SIGLEC-1.

As used in the context of the present invention, a sample is intended to mean a biological sample, which is amenable to protein or nucleic acid analysis. Suitable samples which can be analyzed in accordance with the method of the present invention include a biological fluid such as whole blood or serum. Other examples of biological fluids include plasma, urine, tears, mucus ascites fluid, oral fluid, saliva, semen, seminal fluid, mucus, stool, sputum, cerebrospinal fluid, bone marrow, lymph, and fetal fluid. The biological fluid samples may include cells, proteins, or membrane extracts of cells and may be obtained from a subject (e.g., human, livestock or companion animal) according to standard clinical practices.

The biological sample may also be from tissue specimen, e.g., from the prostate, central nervous system, bone, breast tissue, renal tissue, endometrium, head/neck, gall bladder, parotid tissue, brain, pituitary gland, kidney tissue, muscle, esophagus, stomach, small intestine, colon, urethra, liver, spleen, pancreas, thyroid tissue, heart, lung, bladder, adipose tissue, lymph node tissue, adrenal tissue, testis tissue, tonsils, or thymus.

In one embodiment of this method, the expression of at least one biomarker is measured in assays using a binding agent, which specifically binds to the biomarker protein (i.e., CELA3B or SIGLEC-1) and no other protein. In this embodiment, a sample is contacted with a binding agent (e.g., antibody), which binds the biomarker protein, and the resulting biomarker-binding agent complex is detected using standard assays (e.g., an immunoassay). When the binding agent is, for example, a peptide aptamer, the biomarker-binding agent complex can be directly detected by, for example, a detectable marker protein (e.g., β-galactosidase, GFP or luciferase) fused to the aptamer. Subsequently, the level or amount of the biomarker-binding agent complex is correlated with the presence or absence of a type I diabetes in the sample.

Binding agents for use in accordance with the instant invention include antibodies or antibody fragments, as well as peptide aptamers. In particular embodiments of the invention, the binding agent specifically recognizes CELA3B or SIGLEC-1. When the binding agent is an antibody, the antibody can be purchased from a commercial source. Alternatively, an antibody that specifically binds to or recognizes CELA3B or SIGLEC-1 can be raised against an antigen fragment of CELA3B or SIGLEC-1. Suitable antigenic regions of the CELA3B or SIGLEC-1 protein can be readily identified by the skilled artisan using any art-established computer algorithm for identifying such antigenic sequences (e.g., Jamison and Wolf (1988) *Bioinformatics* 4:181-186; Carmenes, et al. (1989) *Biochem Biophys Res Commun.* 159(2):687-93).

For the production of antibodies, various hosts including goats, rabbits, rats, mice, humans, and others, may be immunized by injection with CELA3B or SIGLEC-1 protein or any fragment or oligopeptide thereof which has antigenic or immunogenic properties. Depending on the host species, various adjuvants can be used to increase the immunological response. Such adjuvants include, but are not limited to, Freund's, mineral gels such as aluminum hydroxide, and surface-active substances such as lysolecithin, pluronic polyols, polyanions, peptides and oil emulsions. Among adjuvants used in humans, BCG (bacilli Calmette-Guerin) and *Corynebacterium parvum* are particularly suitable.

An antibody to CELA3B or SIGLEC-1 can be generated by immunizing an animal with an oligopeptide, peptide, or fragment of the CELA3B or SIGLEC-1 protein. Generally, such oligopeptides, peptides, or fragments have an amino acid sequence composed of at least five amino acid residues and more desirably at least 10 amino acid residues. Fragments of CELA3B or SIGLEC-1 protein can be generated by, for example, tryptic digestion and extraction from a preparative SDS-PAGE gel or by recombinant fragment expression and purification. Further, short stretches of amino acids of CELA3B or SIGLEC-1 antigen can be fused with those of another protein such as keyhole limpet hemocyanin and antibody produced against the chimeric molecule.

Monoclonal antibodies to CELA3B or SIGLEC-1 protein can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell Biol.* 62:109-120).

Moreover, antibodies to CELA3B or SIGLEC-1 protein can be isolated by screening libraries of antibodies or antibody-like molecules, such as Forkhead-Associated (FHA) domains, monobodies, minibodies, AFFIBODY molecules, affilins, anticalins, DARPins (i.e., designed ankyrin repeat proteins), and nanofitins (also known as affitins). Library platforms for screening for antibodies or antibody-like molecules include, but are not limited to, phage display (see, e.g., Benhar & Reiter (2002) *Curr. Protoc. Immunol.* 48:VI:10.19B:10.19B.1-10.19B.31), yeast display (see, e.g., Miller, et al. (2005) *Prot. Expr. Purif.* 42:255-67), and ribosome display (see, e.g., Douthwaite, et al. (2006) *Prot. Eng. Des. Set.* 19:85-90).

In addition, techniques developed for the production of humanized and chimeric antibodies, the splicing of mouse antibody genes to human antibody genes to obtain a molecule with appropriate antigen specificity and biological activity, can be used (Morrison, et al. (1984) *Proc. Natl. Acad. Sci.* 81, 6851-6855; Neuberger, et al. (1984) *Nature* 312:604-608; Takeda, et al. (1985) *Nature* 314:452-454). Alternatively, techniques described for the production of single chain antibodies can be adapted, using methods known in the art, to produce specific single chain antibodies. Antibodies with related specificity, but of distinct idiotypic composition, can be generated by chain shuffling from random combinatorial immunoglobulin libraries (Burton (1991) *Proc. Natl. Acad. Sci.* 88:11120-11123).

Antibodies can also be produced by inducing in vivo production in the lymphocyte population or by screening immunoglobulin libraries or panels of highly specific binding reagents as is well-known in the art (Orlandi, et al. (1989) *Proc. Natl. Acad. Sci.* 86: 3833-3837; Winter, et al. (1991) *Nature* 349:293-299).

Antibodies of use in the method herein include, but are not be limited to, polyclonal, monoclonal, chimeric, single chain, Fab fragments, bispecific scFv fragments, Fd fragments and fragments produced by a Fab expression library. For example, fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed to allow rapid and easy identification of monoclonal Fab fragments with the desired specificity (Huse, et al. (1989) *Science* 254:1275-1281).

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) *Biotechnology* 14:192-196, and U.S. Pat. No. 6,492,123, herein incorporated by reference, can be used.

Various immunoassays can be used for measuring binding of a binding agent to CELA3B or SIGLEC-1 and hence determining the expression of CELA3B or SIGLEC-1. Numerous protocols for competitive binding (e.g., ELISA), latex agglutination assays, immunoradiometric assays, western blot analyses, slot blot assays and kinetics (e.g., BIA-CORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. For a review of the general immunoassays, see also, *Methods in Cell Biology: Antibodies in Cell Biology* (1993) Asai, ed. volume 37; Basic and Clinical Immunology (1991) Stites & Teff, eds. 7th ed.).

Peptide aptamers that specifically bind to CELA3B or SIGLEC-1 protein can be rationally designed or screened for in a library of aptamers (e.g., provided by Aptanomics SA, Lyon, France). In general, peptide aptamers are synthetic recognition molecules whose design is based on the structure of antibodies. Peptide aptamers are composed of a variable peptide loop attached at both ends to a protein scaffold. This double structural constraint greatly increases the binding affinity of the peptide aptamer to levels comparable to that of an antibody (nanomolar range). Likewise, aptamers, which bind to nucleic acid sequences encoding CELA3B or SIGLEC-1 protein, can also be identified in library screens.

In an alternate embodiment of the method of the present invention, the level or amount of CELA3B or SIGLEC-1 in a sample (e.g., samples provided supra) is determined by measuring the level or amount of nucleic acid molecules encoding CELA3B or SIGLEC-1, e.g., mRNA, cRNA, and cDNA or fragments thereof. Nucleic acid molecules encoding CELA3B or SIGLEC-1 can be detected using any available method including, but not limited to, northern blot analysis, nuclease protection assays (NPA), Serial Analysis of Gene Expression (SAGE), RNA Seq, in situ hybridization, reverse-transcriptase PCR, PCR, microarray, tiling arrays and the like. Due to the ease of use, it is generally desirable to detect the nucleic acid molecules using a PCR-based approach. In general, this involves contacting the sample with two or more PCR primers, which specifically hybridize with nucleic acids encoding CELA3B or SIGLEC-1 or which flank the coding region of CELA3B or SIGLEC-1, subjecting the sample to multiple steps of PCR amplification and detecting the amount of the amplified sequence (e.g., using gel analysis, blotting methods, fluorescently labeled probes and/or incorporation of a fluorescent dye that intercalates double stranded DNA such as SYBR Green). Alternatively, an oligonucleotide, an aptamer, a cDNA, an antibody, or a fragment thereof, which interacts with at least a portion of the nucleic acid encoding CELA3B or SIGLEC-1 protein is configured in an array on a chip or wafer and used for detecting nucleic acids encoding CELA3B or SIGLEC-1. Briefly, these techniques involve methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251(4995):767-73).

Primers (e.g., for PCR-based approaches), probes (e.g., for hybridization-based approaches) or oligonucleotides (e.g., for microarray-based approaches) for use in this embodiment can be selected from any region of the locus encoding CELA3B or SIGLEC-1 protein and generally specifically anneal and amplify at least a portion of a nucleic acid molecule encoding CELA3B or SIGLEC-1 and no other nucleic acid molecule encoding a closely related protein. Suitable primers for amplification of nucleic acid molecules encoding CELA3B or SIGLEC-1 can be selected by analyzing the sequences provided by the GENBANK Accession numbers disclosed herein.

In general, suitable primers are 12 to 30 bp in length and generate a PCR amplicon of 50, 100, 200 400, 600, 1000 bp or more in length. In accordance with this method, a geometrically amplified product is obtained only when the first and second nucleotide sequences occur within the same nucleic acid molecule encoding the CELA3B or SIGLEC-1 protein. The fundamentals of non-degenerate PCR are known to the skilled artisan, see, e.g. McPherson, et al., PCR, A Practical Approach, IRL Press, Oxford, Eng. (1991).

In certain embodiments, forward and reverse oligonucleotides or primers of use in the amplification of CELA3B have the sequences 5'-GCA AGA TGC CTG ACT TTC CC-3' (SEQ ID NO:1) and 5'-CCC GAA AGT GGA ATT CAC AGG-3' (SEQ ID NO:2), respectively. In other embodiments, forward and reverse oligonucleotides or primers of use in the amplification of SIGLEC-1 have the sequences 5'-TAG GCC CGG GTG TAG GAT TC-3' (SEQ ID NO:3) and 5'-GAA TTG CCC ATC CGT ACC CT-3' (SEQ ID NO:4), respectively.

Using the method of the invention, levels of type I diabetes biomarkers (i.e., CELA3B and optionally SIGLEC-1 or fragments or variants thereof) are determined in a biological sample from a test subject and in one or more comparable biological samples from normal or healthy subjects (i.e., control samples). A level of type I diabetes biomarker (i.e., CELA3B and optionally SIGLEC-1 or fragments or variants thereof) detected in a biological sample from a test subject that is higher than the type I diabetes biomarker level detected in a comparable biological sample from a normal or healthy subject, indicates that the subject has developed type I diabetes or is likely to develop type I diabetes. In some embodiments, the method of the present invention will also include a positive and/or negative control to assess the accuracy of the method.

In light of the use of the biomarkers herein for identifying whether a subject has or at risk of having type I diabetes, this invention also provides for the prophylactic or therapeutic treatment of a subject to prevent, delay, ameliorate, slow or reverse the development or progression of type I diabetes or complications associated with type I diabetes. In accordance with the therapeutic method, a sample is obtained from a subject; the expression of CELA3B and optionally SIGLEC-1 protein, or nucleic acids encoding the same, is measured in the sample; the expression level or amount of CELA3B and optionally SIGLEC-1 in the sample is compared to the expression level or amount of CELA3B and optionally SIGLEC-1 in a control, e.g., one or more normal, i.e., non-diabetic samples obtained from one or more non-diabetic individuals and the subject is treated for diabetes when the expression of CELA3B and optionally SIGLEC-1 in the sample from the subject is elevated compared to the expression of CELA3B and optionally SIGLEC-1 in the control. In one embodiment, the assay of the present invention is carried out by measuring the expression level or amount of CELA3B. In another embodiment, the assay of the present invention is carried out by measuring the expression level or amount of both CELA3B and SIGLEC-1.

Various approaches for primary, secondary, and tertiary prevention have been suggested. See, e.g., Rewers & Gottlieb (2009) *Diabetes Care* 32:1769-82. In particular, avoidance of environmental triggers of islet autoimmunity such as cow's milk or gluten can slow the development of diabetes, as can a diet supplemented with nutrients for which deficiency presumably promotes islet autoimmunity, e.g., n-3 fatty acids or vitamin D. In addition, antigen-specific "vaccination" using islet autoantigens, e.g., intact insulin, altered insulin or proinsulin peptides, $GAD_{65}$, or heat shock protein 60 (HSP60) peptide can be used to induce autoantigen-specific tolerance. Further, to overcome the relapsing-remitting course of pre-diabetes, β-cell regeneration can be stimulated in conjunction with suppression of apoptosis that is increased in islet autoimmunity. Moreover, anti-CD3 antibody treatment has been suggested to deplete T cells. Similarly, rituximab is a monoclonal antibody that targets the CD20 receptor unique to B-cells. In particular embodiments, a subject at risk of developing or in the early stages of type I diabetes is prophylactically treated with Trichostatin A (TSA).

Therapeutic treatment of a subject can include taking insulin (HUMULIN 70/30, NOVOLIN 70/30, and the like), insulin isophane (HUMULIN N, NOVOLIN N), insulin glulisine (APIDRA), insulin lispro (HUMALOG) and insulin aspart (NOVOLOG), glargine (LANTUS), detemir (LEVEMIR), or pramilintide, carbohydrate counting, eating healthy foods, exercising regularly and maintaining a healthy weight.

The methods of the invention can also be adapted to monitor the effect of an anti-diabetes drug or a therapy administered to the subject diagnosed with diabetes. The effect of an anti-diabetes drug or a therapy administered to a subject with diabetes may include the worsening or improvement of diabetes processes such as inflammation. This also could be used to evaluate the health of beta cells and whether therapy is effective in helping to prevent loss of beta cell mass or help in regeneration or restoration of beta cell mass or function.

In addition, the methods of the invention can include determining biomarker expression at various times after administration of an anti-diabetes drug or a therapy. A type I diabetes biomarker level detected in a biological sample from a subject at a first time (e.g., before giving an anti-diabetes drug or a therapy) that is higher than the type I diabetes biomarker level detected in a comparable biological sample from the same subject taken at a second time (e.g., after giving an anti-diabetes or a therapy), indicates that the diabetes in the subject is regressing. Likewise, a higher type I diabetes biomarker level at a second time compared to a type I diabetes biomarker level at a first time, indicates that the diabetes in the subject is progressing.

In addition to measuring the level or amount of CELA3B and optionally SIGLEC-1, the present invention also contemplates additional molecules that may be important in type I diabetes pathogenesis and could form a panel of potential biomarkers to discriminate between disease and non-disease states. In some embodiments, a first panel can include CELA3B, ELANE (neutrophil elastase), CSF2 (Colony Stimulating Factor 2 (Granulocyte-Macrophage)), and SIGLEC-1, which, compared to non-diabetic individuals, exhibit a very strong, 2-6 log higher expression in subjects at risk of developing type I diabetes and have high expression levels in subjects exhibiting progression of type I diabetes. In other embodiments, a second panel can include TNFA (tumor necrosis factor (TNF superfamily, member 2)), ZNT1 (zinc transporter 1), IFH1H1 (interferon-induced helicase C domain-containing protein 1), and IL17A (interleukin 17A), which exhibit a reduced or lack of expression in subjects at risk of developing type I diabetes. In further embodiments, a third panel can include AHR (aryl hydro carbon receptor), SERPINA (serine peptidase inhibitor A), DNMT1 (DNA methyl transferase 1), DNMT3A (DNA methyl transferase 3A), ZNT8 (zinc transporter 8), IL1B (interleukin 1B), IL6 (interleukin 6), IFNG (interferon gamma), IL12A, (interleukin 12A) and IL27 (interleukin 27), which, compared to controls, have an increase in expression in subjects exhibiting progression of type I diabetes. In some embodiments, the first panel (CELA3B, ELANE, CSF2 and SIGLEC-1) and second panel (TNFA, ZNT1, IFH1H1 and IL17A) are combined to identify subjects at risk of developing type I diabetes. In other embodiments, the first panel (CELA3B, ELANE, CSF2 and SIGLEC-1) and third panel (AHR, SERPINA, DNMT1, DNMT3A, ZNT8, IL1B, IL6, IFNG, IL12A and IL27) are combined to identify subjects exhibiting type I diabetes progression. Oligonucleotides or primers of use in measuring the expression of the above referenced biomarkers are provided in Table 1.

TABLE 1

| Biomarker | | Primer Sequence (5'→3') | SEQ ID NO: |
|---|---|---|---|
| Panel 1 | | | |
| CELA3B | Forward | GCA AGA TGC CTG ACT TTC CC | 1 |
| | Reverse | CCC GAA AGT GGA ATT CAC AGG | 2 |
| ELANE | Forward | GCC AAG TCT GAT CTC CGT GC | 5 |
| | Reverse | GAC AAT CTC TCC CGC CCT TC | 6 |
| CSF2 | Forward | CCA GGC CAG GAA GTC CAA AC | 7 |
| | Reverse | GGC CCT TAT CAG CCA CAC AT | 8 |
| SIGLEC-1 | Forward | TAG GCC CGG GTG TAG GAT TC | 3 |
| | Reverse | GAA TTG CCC ATC CGT ACC CT | 4 |
| Panel 2 | | | |
| TNFA | Forward | AGG ACG AAC ATC CAA CCT TCC CAA | 9 |
| | Reverse | TTT GAG CCA GAA GAG GTT GAG GGT | 10 |
| ZNT1 | Forward | GAG ATG CCT TGG GTT CAG TGA TTG | 11 |
| | Reverse | GGT CAG GGA AAC ATG GAT TCA CAC | 12 |

TABLE 1-continued

| Biomarker | | Primer Sequence (5'→3') | SEQ ID NO: |
|---|---|---|---|
| IFH1H1 | Forward | AGG GAG CTC TGA CTT GAC CA | 13 |
| | Reverse | GGG ACA GCC TTT TTA TGG GGA | 14 |
| IL17A | Forward | GTA AGT GAC CAC AGA AGG AGA AA | 15 |
| | Reverse | CCC AGG AGT CAT CGT TGT TT | 16 |
| Panel 3 | | | |
| AHR | Forward | TGT TCG TAC TGT CCA GGT GA | 17 |
| | Reverse | GAA GGG AGG TGG GTA GCA AA | 18 |
| SERPINA1 | Forward | TGG TGC AGA GCG ATT ATT CAG G | 19 |
| | Reverse | TAA CAG CAG CCA TGA GGG TT | 20 |
| DNMT1 | Forward | CGC ATC CTT ACC TCT GTC CC | 21 |
| | Reverse | ACC CCA GCA TTT GCC GAA TA | 22 |
| DNMT3A | Forward | ACT GGA AGC CTG GAA GTT TAG | 23 |
| | Reverse | ACC TCC TCT CAG ACA AAG GA | 24 |
| ZNT8 | Forward | GGT GGT GAC TGG CGT GCT A | 25 |
| | Reverse | CCA CTG CGC AGC TGG AA | 26 |
| IL1B | Forward | CAC TCC AGG CAC TGT TCA TAA | 27 |
| | Reverse | TAA CCG AGA CAC CAG CAA AG | 28 |
| IL6 | Forward | GCC TGC ATT AGG AGG TCT TT | 29 |
| | Reverse | CCT GAC ACC AGC AAA GGA TAA | 30 |
| IFNG | Forward | CGA TAT GAA CCA CCT GGA GAG G | 31 |
| | Reverse | ACG GAG TCA GAT TTT CCC CG | 32 |
| IL12A | Forward | CCA CAA GCC CTC TGA GAG TC | 33 |
| | Reverse | TTG ACA AGG TGT GGC CAA GT | 34 |
| IL27 | Forward | AGT TCA CAG TCA GCC TGC AT | 35 |
| | Reverse | CAG GTG AGA TTC CGC AAA GC | 36 |

In conjunction with the diagnostic and treatment method of the present invention, a kit for measuring the expression of one or more biomarkers disclosed herein is also provided. A kit of the invention includes a container containing at least one binding agent (e.g., an antibody), which specifically binds CELA3B or SIGLEC-1 protein. Alternatively, the kit contains suitable oligonucleotides or probes for hybridization or primers for amplifying nucleic acids encoding CELA3B or SIGLEC-1. In one embodiment, the kit includes forward and reverse oligonucleotides or primers for CELA3B, which have the sequences 5'-GCA AGA TGC CTG ACT TTC CC-3' (SEQ ID NO:1) and 5'-CCC GAA AGT GGA ATT CAC AGG-3' (SEQ ID NO:2), respectively. In other embodiments, the kit includes forward and reverse oligonucleotides or primers for SIGLEC-1, which have the sequences 5'-TAG GCC CGG GTG TAG GAT TC-3' (SEQ ID NO:3) and 5'-GAA TTG CCC ATC CGT ACC CT-3' (SEQ ID NO:4), respectively. The kit can also contain other solutions necessary or convenient for carrying out the invention. The container can be made of glass, plastic or foil and can be a vial, bottle, pouch, tube, bag, etc. The kit may also contain written information, such as procedures for carrying out the present invention or analytical information, such as the amount of reagent contained in the first container means. The container can be in another container, e.g., a box or a bag, along with the written information.

In one embodiment, the kit includes a solid support, such as a chip, a microtiter plate or a bead or resin having a capture reagent (e.g., an antibody or oligonucleotide) attached thereon, wherein the capture reagent binds a biomarker of the invention or nucleic acid encoding the same. The kit can also include a washing solution or instructions for making a washing solution, in which the combination of the capture reagent and the washing solution allows capture of the biomarker or biomarker nucleic acids on the solid support for subsequent detection. The kit may include more than one type of adsorbent, each present on a different solid support.

In addition to diagnosis, the biomarkers described herein can be used as therapeutic targets for prevention or treatment of type I diabetes or complications associated therewith. In particular, it is contemplated that the expression of CELA3B and/or SIGLEC-1 can be reduced in a subject diagnosed with type I diabetes thereby preventing or treating the disease. For example, a polynucleotide-based gene expression inhibitor that specifically targets nucleic acids encoding CELA3B or SIGLEC-1 can be used to induce sequence-specific degradation or inhibition of the function, transcription, or translation of CELA3B or SIGLEC-1. Polynucleotide-based expression inhibitors include, e.g., siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA have a double-stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, which direct destruction or translational repression of their mRNA targets. Antisense polynucleotides are molecules that are complimentary to a gene or mRNA. Antisense polynucleotides include, but are not limited to, morpholinos, 2'-O-methyl polynucleotides, DNA, RNA and the like. The polynucleotide-based expression inhibitor may be synthesized in vitro, by recombinant methods, and/or contain chimeric sequences. The polynucleotide-based expression inhibitor may contain ribonucleotides, deoxyribonucleotides, synthetic nucleotides, or any suitable combination such that the target RNA and/or gene is inhibited.

The following non-limiting examples are provided to further illustrate the present invention.

Example 1

Gene Expression Analysis in Mice with T1D

It has been demonstrated that the injection of the well-characterized histone deacetylase inhibitor, Trichostatin A (TSA) prevents the development of T1D in genetically susceptible stain of mice, NOD (Patel, et al. (2011) *Immunol. Cell Biol.* 89:640-649). Genome-wide gene expression profiling using high density DNA microarrays revealed that protection against T1D was accompanied by altered gene expression in immune cells (Jayaraman, et al. (2013) *PLoS One* 8:e55074). Based on this analysis, a set of pro-inflammatory genes, notably elastase, was over-expressed in NOD mice, which, like humans, develop T1D spontaneously. The inverse correlation between the expression level of elastase and protection against T1D was validated by qRT-PCR (Jayaraman, et al. (2013) *PLoS One* 8:e55074). Importantly, treatment with TSA provided robust protection against T1D (Patel, et al. (2011) *Immunol. Cell Biol.* 89:640-649; Jayaraman, et al. (2013) *PLoS One* 8:e55074) and significantly lowered the expression of the elastase gene in both the peripheral lymphoid organ spleen and in the target organ pancreas (Jayaraman, et al. (2013) *PLoS One* 8:e55074). Moreover, administration TSA did not result in obvious side effects or gross pathological changes associated with drug administration. Indeed, TSA treatment was accompanied by eradication of inflammation surrounding the islets of Langerhans by clearing of the inflammatory cells and preservation of the beta cells producing the insulin hormone (Patel, et al. (2011) *Immunol. Cell Biol.* 89:640-649; Jayaraman, et al. (2013) *PLoS One* 8:e55074). Therefore, these data demonstrate the utility of TSA to block the progression of this disease when given at the prediabetic stage (prior to developing full blown diabetes). As such, TSA is a viable strategy to prevent the manifestation of T1D.

To understand the molecular mechanisms underlying protection against T1D bestowed by TSA treatment in NOD/Ltj mice, transcriptome (gene expression profiling) of spleen cells was analyzed by global gene expression profiling using a microarray approach. To this end, total RNA was isolated from diabetic and cured mice, converted into cRNA and then hybridized to AFFYMETRIX GENECHIP Mouse Genome 430 2.0 microarrays that contain 45,000 probe sets representing 34,000 mouse genes. Three-way analysis of gene expression in untreated-non-diabetic mice, overtly diabetic mice, and those cured by TSA treatment yielded 164 differentially regulated genes, filtered by an ANOVA p-value, 0.05. These highly regulated genes were used for hierarchical clustering. Microarray data sets were deposited at Gene Expression Omnibus (accession no. GSE 26461) (Jayaraman, et al. (2013) *PLoS One* 8:e55074).

Further analysis indicated that a distinct, non-overlapping set of genes (n=17) was over-expressed in spleens of acutely diabetic mice, which were repressed by TSA treatment. Principal component analysis validated the up-regulation of a set of pro-inflammatory genes in uninduced spleens of overtly diabetic mice, and their repression by TSA treatment. This analysis clearly distinguished the genes that may be responsible for T1D manifestation and therefore of significant impact on the diagnosis of T1D in humans (Jayaraman, et al. (2013) *PLoS One* 8:e55074).

Expression levels of selected top hit genes were verified in spleens by quantitative real time-PCR using primer sets that were validated following MIQE guidelines and RNA derived from spleens of mice that were different from those used for microarray analysis. The expression of inflammatory genes such as Cela3b (elastase 3), Cpb1 (carboxyepetidase B1), Pnlip (pancreatic lipase) and Cel (carboxyl ester lipase) was prominent in the spleens of diabetic mice. In stark contrast, TSA treatment reduced the expression levels of these genes substantially. However, Ctrl (chymotrypsin-like) gene substantially over-expressed in the exocrine pancreas was not repressed by TSA treatment, indicating the selectivity of gene regulation by chromatin remodeling in the pancreata. In addition, the mRNA levels of Pnliprp-1 (pancreatic lipase-related protein 1), Pnlilrp-2, Ctrl, Ctrc and Cpa1 were not altered by TSA treatment. These data validate the data obtained by microarray analysis (Jayaraman, et al. (2013) *PLoS One* 8:e55074).

GeneMania prediction analysis indicates that Cela3b is functionally related to lipases such as Pnliprp1, Pnliprp2, Cel and Pnilp. Importantly, these genes were also down-regulated along with Cela3b by TSA treatment. On the other hand, while Cela3b can also interact with peptidases, peptidases were not co-regulated with the elastase gene, suggesting that these peptidases may not be functionally involved in the manifestation of T1D (Jayaraman, et al. (2013) *PLoS One* 8:e55074).

Insulin-producing beta cells can be destroyed by the inflammatory cells and the pro-inflammatory genes that were identified by microarray analysis and further validated by quantitative RT-PCR. Therefore, it was determined whether amelioration of T1D by TSA treatment involves alteration in the frequency of innate immune cells that are likely to express the Cela3b gene. Therefore, T1D susceptible NOD mice were injected with TSA before the clinical onset of diabetes, starting between 18 and 24 weeks of age, and spleen cells were stained with fluorochrome-labeled antibodies and analyzed by flow cytometry. The numbers of both macrophages of the CD11b+Ly6C+ phenotype and neutrophils expressing CD11b+Ly6G+ determinants, known to exert inflammatory responses and tissue damage, increased in the spleen of overtly diabetic mice when compared to prediabetic mice. Importantly, treatment with TSA ameliorated diabetes and reduced the frequency of both CD11b+Ly6C+ macrophages and CD11b+Ly6G+ neutrophils. On the other hand, TSA treatment did not affect the frequency of CD11b+F4/80+ macrophages. Essentially, the same numbers of dendritic cells expressing CD11c determinant were found in the spleens of prediabetic mice, diabetic mice and those treated with TSA and cured of diabetes. Thus, these data demonstrate that the effect of TSA is restricted to the inflammatory compartment of the immune system and does not affect cells crucial for normal immune responses.

It was next investigated whether there was a correlation between the numbers of inflammatory cells expressing elastase and the health status. To this end, spleen cells from diabetic mice and those treated with TSA and cured of diabetes were surface labeled with FITC labeled anti-Ly6C antibody (to stain macrophages) and anti-Ly6G antibody (to stain neutrophils). After staining, cells were fixed, permeabilized and incubated with rabbit antibody against elastase, followed by treatment with TRITC-labeled goat anti-rabbit antibody. Cells were analyzed by flow cytometry for the cell surface expression of Ly6C or Ly6G and these cells were gated and analyzed for the intracellular expression of elastase. This analysis indicated that spleens from diabetic mice contained ~10% Ly6C+ cells that co-expressed elastase. Importantly, spleens from mice that were cured of diabetes had significantly lower numbers of Ly6C+ macrophages that contained elastase in the cytoplasm. Similarly, the numbers of Ly6G+ neutrophils co-expressing elastase protein were also diminished in TSA treated and cured mice. Thus, TSA treatment abrogated spontaneously occurring T1D in NOD mice, which was negatively correlated with the frequency of both Ly6C+ macrophages and Ly6G+ neutrophils that co-express elastase.

To visualize the localization of elastase, spleen cells from diabetic mice were incubated with FITC-labeled antibody against Ly6C, fixed, permeabilized, incubated with rabbit antibody against elastase followed by TRITC-labeled goat anti-rabbit antibody. Cells were imaged on a confocal microscope and the images were analyzed. This analysis indicated that Ly6C expression was restricted to the plasma membrane whereas elastase was expressed throughout the cytoplasm, excluding the nucleus. Further, it was observed that Ly6G+ neutrophils also expressed cytoplasmic elastase similar to macrophages. Thus, elastase expression is evident both in Ly6C+ macrophages and in the Ly6G+ neutrophils that can cause damage to beta cells.

To establish the role of macrophages in mediating T1D, CD4+ T cells and macrophages were purified from overtly diabetic mice and then adoptively transferred into immunodeficient NOD.scid mice. Although NOD.scid mice are identical to NOD/Ltj mice, they lack T cells, B cells and macrophages and hence are unable to manifest T1D. The results of this analysis demonstrated that the adoptive transfer of T cells ($5\times10^6$ CD4+) from diabetic mice did not mediate T1D but the combination of T cells and the Ly6C+ macrophages ($5\times10^5$) readily induced the disease in NOD-.scid mice. However, transfer of macrophages alone failed to cause diabetes. Injection of whole spleen cells, which contain T cells and macrophages, induced diabetes. These data demonstrate that Ly6C+ macrophages play a crucial role in the establishment of T1D mediated by T cells in the mouse model.

To visualize the effect of TSA treatment on the infiltration of inflammatory cells in the pancreas, paraffin-embedded pancreatic sections were treated with antibodies against insulin, Ly6C+ macrophages and Ly6G+ neutrophils. Sections were then imaged on a confocal microscope and the images analyzed. Both Ly6C+ macrophages and Ly6G+ neutrophils were evident in the islets of diabetic mice, as identified by co-staining with an anti-insulin antibody. In contrast, both Ly6C+ macrophages and Ly6G+ neutrophils were absent in the islets of drug-treated and cured mice. These data collectively demonstrate that macrophages and neutrophils infiltrate the pancreas leading to the destruction of insulin-producing beta cells and eventually cause diabetes. Treatment with TSA effectively eradicated the infiltration of inflammatory cells and thereby provides protection against T1D in the mouse model. These results indicate that inflammatory cells expressing elastase can mediate diabetes and their regulation can lead to protection against T1D.

Example 2

Gene Expression Analysis in Humans with T1D

Gene Expression in Newly Diagnosed and Long-Standing T1D Patients. Differential gene expression was also determined in a small cohort of T1D patients. Both males and females of Caucasian and Hispanic background, who were diagnosed with T1D for varying periods of time and were on medication for diabetes management, were recruited for this study. They were divided into two groups based on their age: Five were less than 18 years of age and two were >18 years old. Those that were less than 18 years of age were highly likely to represent 'newly diagnosed' T1D patients, whereas those older than 18 years of age had T1D for a longer period and hence designated as 'long-standing' T1D patients. Normal individuals, who were non-diabetic and apparently healthy, served as controls.

Fasting peripheral blood was obtained by a venipuncture and collected in tubes containing EDTA to prevent clotting. The tubes containing blood were then centrifuged at 2,000 RPM for 15 minutes to sediment red blood cells. The top layer, termed the buffy coat containing both mononuclear and polymorphonuclear cells minus the red blood cells, was aspirated and stored in individual tubes at −80° C. until used. Total RNA was extracted from all of these samples. This was achieved by individually lysing the buffy coat samples in TRIZOL and adding chloroform to dissolve lipids. The mixture was then centrifuged for 15 minutes at 13,000 RPM according to standard methods (Patel, et al. (2011) *Immunol. Cell Biol.* 89:640-649; Jayaraman, et al. (2013) *PLoS One* 8:e55074). The clear supernatant containing total RNA was collected and transferred to fresh tubes containing absolute ethanol and kept at −80° C. to precipitate RNA overnight. The RNA was pelleted and then washed with 70% alcohol, air-dried, and reconstituted in water free of DNases, RNases, and proteinases. RNA amounts were estimated and the RNA was subsequently treated with DNase A to remove the contaminating genomic DNA. DNA-free RNA was converted into complementary DNA and specific genes were amplified by qRT-PCR according to established methods (Patel, et al. (2011) *Immunol. Cell Biol.* 89:640-649; Jayaraman, et al. (2013) *PLoS One* 8:e55074; Jayaraman & Jayaraman (2011) *J. Nutr. Biochem.* 22:79-88). All of the primer sets used in this study were designed for gene quantification and validated following MIQE guidelines. For the quantification of some genes, known primer sets were used (Jayaraman & Jayaraman (2011) *J. Nutr. Biochem.* 22:79-88). The level of individual gene expression was determined in triplicate per sample and calculated using the comparative threshold cycle ($2^{-\Delta\Delta C_T}$) method as described (Patel, et al. (2011) *Immunol. Cell Biol.* 89:640-649; Jayaraman, et al. (2013) *PLoS One* 8:e55074; Jayaraman & Jayaraman (2011) *J. Nutr. Biochem.* 22:79-88). Outliers were removed from analysis and the level of gene expression was calculated relative to the house keeping gene, GAPDH, which remains constant regardless of the pathological conditions. The level of expression of each gene in individuals belonging to the same group were combined and expressed as the mean±standard error. Statistical significance ($P<0.05$) between the expression levels of each gene among the three groups was determined using the statistical package (GraphPad Prism).

This analysis indicated that the unstimulated and hence resting peripheral blood leukocytes from both the newly diagnosed (<18 years of age) and long-lasting (>18 years old) T1D patients robustly expressed the macrophage associated elastase (ELA3B) as observed in mice. Although the expression of neutrophil elastase (ELANE) was increased in T1D patients, it did not reach statistical significance. Similarly, the gene encoding the colony stimulating factor-(CSF-2), implicated in several pathological conditions was also increased in T1D patients but not significantly. However, SIGLEC-1 (sialic acid binding Ig-like lectin) implicated in autoimmune disease like multiple sclerosis and rheumatoid arthritis was also over-expressed in both populations of T1D patients by several fold. Therefore, the expression of ELA3B and SIGLEC-1 appears to be intimately associated with the onset of T1D.

The expression of genes such as TNFA, a powerful cytokine involved in numerous pathological conditions; ZNT1, a zinc transporter known to be over-expressed in pancreatic cancer cells (Jayaraman & Jayaraman (2011) *J. Nutr. Biochem.* 22:79-88); and IFH1H1 (interferon-induced helicase C domain-containing protein 1), implicated in certain pathological conditions were also analyzed. The expression of these genes was found to be enhanced in long-standing T1D patients but was reduced in the recent onset T1D patients. Interestingly, the IL-17A gene displayed the reverse pattern of expression; it was reduced significantly in long-standing T1D patients. Thus, a second group of genes, designated group II, represented by TNFA, ZNT1, and IFH1H1 appear to serve as enhancers of T1D. Screening for increased expression of these genes in addition to reduced expression of IL17A can provide clues as to who may develop full-blown diabetes in seropositive individuals with high risk of developing the disease.

Surprisingly, both recent onset and long-standing T1D patients did not express many genes which play many important biological roles including AHR (aryl hydro carbon receptor), which responds to environmental pollutants as well as undefined endogenous signals; ZNT8, a zinc transporter thought to be expressed exclusively by insulin-producing beta cells (Jayaraman & Jayaraman (2011) *J. Nutr. Biochem.* 22:79-88); SERPINA (serine peptidase inhibitor A); DNA methyl transferase 1 (DNMT1), responsible for de novo DNA methylation; and DNMT3A, implicated in methylating promoters of cytosine genes during DNA replication, which leads to gene silencing. In addition, the expression of immune response genes such as IFNG, IL1B, IL6, IL12A, and IL27 was undetectable in T1D patients. The lack of expression of this fairly large set of genes (i.e., AHR, ZNT8, SERPINA, DNMT1, DNMT3A, IFNG, IL1B, IL6, IL12A, and IL27) was uniform in both newly diagnosed and long-standing T1D patients, indicating that these genes may not necessarily be involved in the onset and/or manifestation of T1D but rather may bestow individuals with resistance to T1D.

Gene Expression in T1D Patients as Compared to Healthy Controls.

Data obtained in the mouse model suggested that elastase gene expressed in a subset of (Ly6C+) macrophages is critically involved in the manifestation of T1D. Importantly, elastase repression both at the level of gene transcription, as assessed by quantitative RT-PCR, and at the protein level, as determined by imaging and flow cytometry based studies, suggests that the level of expression of this gene could serve as a viable biomarker for the diagnosis of T1D in humans as well. Accordingly, the level of expression of a number of selected genes (n=12) that could contribute to the induction and manifestation of T1D was analyzed. A total of 18 patients with T1D were recruited to this study. Fasting peripheral blood samples were obtained from these patients (n=18) and non-diabetic healthy volunteers (n=6). Total RNA was extracted from the buffy coat and converted to cDNA, which was used for quantifying gene expression using primer sets and qRT-PCR analysis. The levels of genes were expressed with reference to the house keeping gene, GAPDH. Out of the 12 genes interrogated (CELA3B, ELANE, CSF2, SIGLEC-1, TNFA, ZNT1, IFH1HA, IL17A, AHR, SERPINA, DNMT1, and DNMT3A), the macrophage-specific elastase gene (CELA3B) was the most highly expressed by at least 5 logs in all patients with T1D (n=18; FIG. 1). Interestingly, SIGLEC-1 (Sialic acid-binding immunoglobulin-like lectin), which is involved in multiple steps of the immune response, was also significantly upregulated at least by 2 logs in T1D patients (FIG. 1). In contrast, the neutrophil specific elastase gene, ELANE was not significantly upregulated in comparison with normal healthy individuals. This was distinct from the analysis of elastase protein expression in mouse cells discussed in Example 1. Furthermore, the level of expression of CSF2, (granulocyte macrophage colony stimulating factor-GM-CSF), important for the propagation of granulocytes and macrophages, was also not significantly overexpressed in T1D patients. Thus, the over-expression of CELA3B by more than 5-logs consistently in uninduced peripheral blood leukocytes indicates that macrophage-specific CELA3B, either alone or in combination with SIGLEC-1, serves as a reliable biomarker for the diagnosis of T1D in humans.

What is claimed is:

1. A method for diagnosing a subject with type diabetes comprising
   (a) obtaining a sample from the subject;
   (b) measuring the expression of Chymotrypsin-Like Elastase Family, Member 3B (CELA3B) and optionally sialic acid-binding immunoglobulin-like lectin-1 (SIGLEC-1) in the sample, wherein the expression of CELA3B is measured using oligonucleotides consisting of SEQ ID NO: 1 and SEQ ID NO: 2;
   (c) comparing the expression of CELA3B and optionally SIGLEC-1 in the sample to the expression of CELA3B and optionally SIGLEC-1 in a control; and
   (d) diagnosing the subject with type I diabetes when the expression of CELA3B and optionally SIGLEC-1 in the sample from the subject is elevated compared to the expression of CELA3B and optionally SIGLEC-1 in the control.

2. The method of claim 1, wherein the expression of SIGLEC-1 is measured using oligonucleotides of SEQ ID NO:3 and SEQ ID NO:4.

3. A method for treating a subject diagnosed with type I diabetes comprising
   (a) obtaining a sample from the subject;
   (b) measuring the expression of Chymotrypsin-Like Elastase Family, Member 3B (CELA3B) and optionally sialic acid-binding immunoglobulin-like lectin-1 (SIGLEC-1) in the sample, wherein the expression of CELA3B is measured using oligonucleotides consisting of SEQ ID NO: 1 and SEQ ID NO: 2;
   (c) comparing the expression of CELA3B and optionally SIGLEC-1 in the sample to the expression of CELA3B and optionally SIGLEC-1 in a control; and
   (d) treating the subject for diabetes when the expression of CELA3B and optionally SIGLEC-1 in the sample from the subject is elevated compared to the expression of CELA3B and optionally SIGLEC-1 in the control.

4. The method of claim 3, wherein the expression of SIGLEC-1 is measured using oligonucleotides of SEQ ID NO:3 and SEQ ID NO:4.

5. A kit comprising oligonucleotides consisting of SEQ ID NO:1 and SEQ ID NO:2.

6. The kit of claim 5, further comprising oligonucleotides consisting of SEQ ID NO:3 and SEQ ID NO:4.

* * * * *

UNITED STATES PATENT AND TRADEMARK OFFICE
CERTIFICATE OF CORRECTION

PATENT NO.         : 9,850,538 B2
APPLICATION NO.    : 14/684707
DATED              : December 26, 2017
INVENTOR(S)        : Sundararajan Jayaraman Page 1 of 1

It is certified that error appears in the above-identified patent and that said Letters Patent is hereby corrected as shown below:

In the Claims

Column 29, Line 21:
Delete "type diabetes"
Insert -- type I diabetes --

Signed and Sealed this
First Day of May, 2018

Andrei Iancu
*Director of the United States Patent and Trademark Office*